(12) United States Patent
Yokota et al.

(10) Patent No.: US 6,528,705 B1
(45) Date of Patent: Mar. 4, 2003

(54) METHOD FOR IMPROVING PRODUCTIVITY OF HIGHER PLANTS

(75) Inventors: Akiho Yokota, Ikoma (JP); Shigeru Shigeoka, Sakai (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/468,407

(22) Filed: Dec. 20, 1999

(30) Foreign Application Priority Data

Mar. 10, 1999 (JP) .............................................. 11-62891

(51) Int. Cl.$^7$ ........................ C12N 15/09; C12N 15/31; C12N 15/82; A01H 5/00

(52) U.S. Cl. ........................ 800/290; 800/278; 800/288; 800/298; 435/69.1; 435/419; 435/468; 435/430; 435/430.1; 536/23.1; 536/23.2; 536/23.7

(58) Field of Search ................................ 800/278, 288, 800/298, 290; 435/69.1, 468, 430, 419, 430.1; 536/23.1, 23.2, 23.7

(56) References Cited

U.S. PATENT DOCUMENTS 5,693,507 A    12/1997   Daniell et al.

FOREIGN PATENT DOCUMENTS

DE       19502053 A1    7/1996
WO       WO98/58069 A1  12/1998

OTHER PUBLICATIONS

Broun et al. "Catalytic Plasticity of Fatty Acid Modification Enzymes Underlying Chemical Diversity of Plant Lipids", Nov. 1998, Science vol. 282 pp. 1315–1317.*

Lazar et al "Transforming Growth Factor x:Mutation of Aspartic Acid 47 and Leucine 48 Results in Different Biological Activities", Mar. 1988, Molecular and Cellular Biology vol. 8 No. 3 pp. 1247–1252.*

European Search Report (EPO Form 1503) for EP 9912 5331, Completed by the European Patent Office, Mailed Jul. 12, 2002.

Masahiro Tamoi et al., "Molecular Characterization and Resistance to Hydrogen Peroxide of Two Fructose–1, 6–bisphosphatases from Synechococcus PCC 7942[1]", Archives of Biochemistry and Biophysics, vol. 334, No.1, pp. 27–36, Article No. 0425 (Oct. 1996).

Christine A. Raines et al., "New Insights into the Structure and Function of Sedoheptulose–1,7–bisphosphatase; an Important but Neglected Calvin Cycle Enzyme", Journal of Experimental Botany, vol. 50, No. 330, pp. 1–8 (Jan. 1999).

Elizabeth P. Harrison et al., "Reduced Sedoheptulose–1, 7–bisphosphatase levels in Transgenic Tabacco Lead to Decreased Photosynthetic Capacity and Altered Carbohydrate Accumulation", Planta, 204: 27–36 (1998).

Masahiro et al., "Molecular Characterization and Resistance to Hydrogen Peroxide of Two Fructose–1,6–bisphosphatases from Synechococcus PCC 7942", Archives of Biochemistry and Biophysics, vol. 334, No. 1, Oct. 1, 1996, pp. 27–36, Academic Press, Inc., USA.

* cited by examiner

*Primary Examiner*—Amy J. Noh
*Assistant Examiner*—Medina A. Ibrahim
(74) *Attorney, Agent, or Firm*—Burns, Doane, Swecker & Mathis, LLP

(57) ABSTRACT

The present invention relates to a method to improve the primary metabolism of a higher plant having chloroplasts by expressing fructose-1,6-bisphosphatase/sedoheptulose-1,7-bisphosphatase derived from *Cyanobacterium synechococcus* in the chloroplasts. The invention further relates to transgenic plants comprising DNA encoding fructose-1,6-bisphosphatase/sedoheptulose-1,7-bisphosphatase derived from *Cyanobacterium synechococcus*.

10 Claims, 6 Drawing Sheets

Comparison of plant bodies of
a wild type strain (left) and a transgenic plant (right).

Comparison of the blades and stems of
a wildtype strain (left) and a transgenic strain (right).

Comparison of roots of a wild type strain (left) and a transgenic strain (right).

Comparison of the content of the metabolite intermediate hexose produced by photosynthesis.

Comparison of the content of the metabolite intermediate sucrose produced by photosynthesis.

METHOD FOR IMPROVING PRODUCTIVITY OF HIGHER PLANTS

BACKGROUND OF THE INVENTION

1. Field of the Invention

This invention relates to a method for enhancing the photosynthetic activity and growth of a higher plant to increase its harvest yield and/or to enable its earlier harvest.

2. Description of Related Art

The development of a recombinant DNA technique has realized the incorporation of a certain exogenous gene into a higher plant and expression regulation of an existing gene therein. Only few experiments has been attempted to improve the characteristics concerning food production, such as the production yield of serials and crops. Recently, incorporation of a gene, coding enzyme participating in photosynthesis or carbohydrate metabolism, was achieved. Such gene was incorporated in anti-sense direction to inhibit the expression of the gene. The results indicated functional importance of the enzyme as a rate-determining factor of photosynthesis or carbohydrate metabolism. A Researcher in Germany have played a major role in the research.

SUMMARY OF THE INVENTION

Despite of it, no attempts have been performed on phenotypic expression of a certain gene in a higher plant using recombinant DNA technique to enhance the photosynthesis, which is a primary metabolism of a higher plant, and to improve its growth.

The object of this invention is to achieve phenotypic expression of a certain gene in a higher plant using recombinant DNA technique to enhance the photosynthesis, which is primary metabolism of a higher plant, to improve the crop productivity and yield potentiality and/or to enable the earlier harvest of the crop.

This invention provides a method for improving the productivity of a higher plant having chloroplasts by the phenotypic expression of cyanobacterial fructose-1,6-bisphosphatase/sedoheptulose-1,7-bisphosphatase in the chloroplasts.

Moreover, this invention provides a transgenic plant comprising a higher plant with a DNA fragment incorporated therein, the DNA fragment containing a base sequence coding cyanobacterial fructose-1,6-bisphosphatase/sedoheptulose- 1,7-bisphosphatase.

The fructose-1,6-bisphosphatase (FBPase) and sedoheptulose-1,7-bisphosphatase (SBPase) in the chloroplasts of a higher plant are the key (rate determining) enzymes of a photosynthetic reductive carbon system. The activities of these enzymes are regulated by photoreduction-potentiality. On the other hand, fructose-1,6-bisphosphatase/sedoheptulose-1,7-bisphosphatase (FBPase/SBPase), derived from *Cyanobacterium synechococcus* PCC 7942 gene, if found widely in a specific type of a prokaryotic algae—a Cyanobacterium. The primary structure and enzyme properties of cyanobacterial FBPase/SBPase are different from those of the FBPase or SBPase found in the chloroplasts of a higher plant. In addition, cyanobacterial FBPase/SBPase is composed of one protein, that is, a bi-functional enzyme exhibiting two kinds of enzyme activities, FBPase and SBPase.

FBPase-I, derived from *Cyanobacterium synechococcus* PCC 7942 gene, is a tetramer consisting of four subunits of 40 kDa identical with each other. After the treatment by 1 mM $H_2O_2$, the purified enzyme retained more than 80 % of native enzyme activity. The enzyme activity of FBPase-I was inhibited by AMP (Ki=0.26 mM), which is a specific inhibitor of cytoplasm-type FBPase. However, it was not inhibited by fructose-2,6-$P_2$. The optimum pH for the enzyme activity was 8.0 and pI value of the enzyme was 4.8. FBPase-I hydrolyzed not only fructose-1,6-bisphosphate (Fru1,6-$P_2$), but also sedoheptulose-1,7-bisphosphate (Sed1,7-$P_2$). The activities of the purified enzyme for Fru1,6-$P_2$ and Sed1,7-$P_2$ were 11.7 $\mu$mol/min/mg protein and 12.1 $\mu$mol/min/mg protein, respectively. The Km values for Fru1,6-$P_2$ and Sed1,7-$P_2$ were 52 $\mu$M and 118 $\mu$M, respectively. The enzyme activity was proved to be dependent on $Mg^{2+}$ concentration, also equally to typical FBPase. The dose-response curve showed sigmoidal curve equally to plastid FBPase, and the $S_{0.5}$ value was shown to be 1.4±0.1 mM. This enzyme itself was described in "Archives of Biochemistry and Biophysics, Vol. 334, No. 1, pp. 27 to 36, 1996: Molecular characterization and resistance to hydrogen peroxide of two fructose-1,6-bisphosphatase from synechococcus PCC 7942".

The inventor incorporated fructose-1,6-bisphosphatase/sedoheptulose-1,7-bisphosphatase, isolated from *Cyanobacterium synechococcus* PCC 7942, into a tobacco plant so that the expressed protein was transferred to its chloroplasts. The FBPase activity, the SBPase activity and the photosynthetic ability of the transgenic plant were compared to those of the wild type strain. The results measured 7 weeks after seeding showed significant increase of these activities in the transgenic plant. Furthermore, after certain period of cultivation, the plant bodies of the transgenic plant proved to be taller than those of the wild type strain. In the transgenic plant, the areas of the blades, the diameters of the stalks, and the numbers and lengths of the roots were larger than those in the wild type strain. In addition, the contents of hexose, sucrose and starch were proved to be increased in blades, stalks and roots of the transgenic plant, compared with those of the wild type strain.

Accordingly, the photosynthetic ability of the transgenic plant, obtained by incorporation of cyanobacterial FBPase/SBPase into a tobacco plant, was improved. As the result, the ability of the transgenic plant to synthesize carbohydrate and starch is increased, and the growth was enhanced, indicating the increase of final anabolism of the transgenic plant. Therefore, incorporation of cyanobacterial FBPase/SBPase into the chloroplasts of a higher plant was proved to be a very effective technique for producing rareripe or high-yield plants.

The effect might be explained as follows. Triggered by environmental stresses, light and oxygen toxicity causes various kinds of injuries to plant bodies, resulting in a critical and limiting factor of food production. Contrary to FBPase and SBPase derived from a higher plant, cyanobacterial FBPase/SBPase is resistant against oxygen injury and thus considered to function under various environmental stresses. Moreover, a gene encoding the cyanobacterial FBPase/SBPase does not exist in higher plants, thereby eliminating the possibility of adverse effects by gene silencing.

In this invention, a vector to produce a recombinant DNA includes plasmids pBI101, pIN19 and pMSH-1. A wide variety of useful cultivated plants and woods capable of photosynthesis can be adopted as a higher plant in which the inventive recombinant DNA is incorporated. For example, the invention may be applied to serials such as maize, rice, wheat, barley, oat wheat, millet and barnyard millet, beans such as soy bean, vegetables such as potato and tomato, useful cultivated plants such as coleseed, cotton and tobacco, and trees.

An amino acid sequence may be deleted from or added to the amino acid sequence of sequence number 1, or a part of the sequence of the sequence number 1 may be substituted with another amino acid sequence in the scope of this invention, so far as the resulting peptide retains its enzymatic activity properties as fructose-1,6-bisphosphatase/sedoheptulose-1,7-bisphasphatase. Preferably, not lower than 85 percent, more preferably not lower than 95 percent of the amino acid sequence may be overlapped or identical with the amino acid sequence of the sequence number 1.

In a base sequence of sequence number 2, a base sequence referred to as base numbers from 1 to 1068 is essential for this invention, because this base sequence corresponds to a structural gene portion, that is, an amino acid sequence of the sequence number 1. In addition, a base sequence referred to as base numbers from −180 to 1170 is the most preferred embodiment of this invention.

These and other features and advantages of this invention will become apparent upon a reading of the detailed description and drawings.

BRIEF DESCRIPTION OF THE DRAWINGS

FIG. 7a is a comparison of the content of the metabolite intermediate hexose produced by photosynthesis. FIG. 7b is a comparison of the content of the metabolite intermediate sucrose produced by photosynthesis. FIG. 7c is a comparison of the content of the metabolite intermediate starch produced by photosynthesis.

DETAILED DESCRIPTION OF EMBODIMENTS

Figure 1:
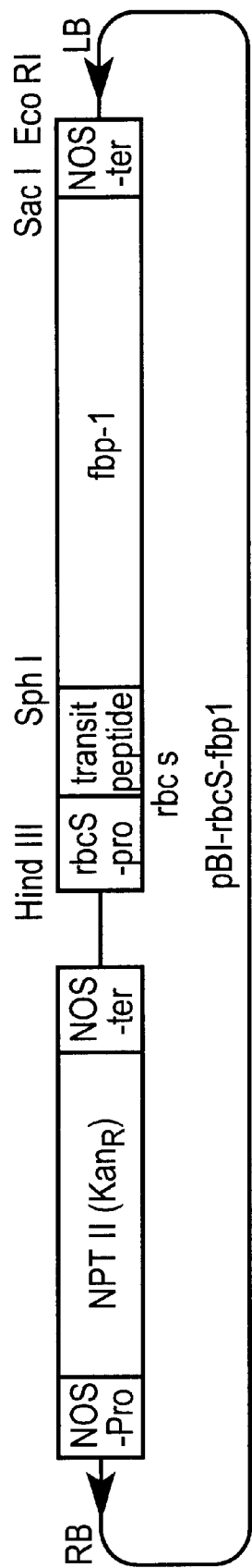
FIG. 1 is a schematic view showing the structure of a plasmid incorporated into tobacco chloroplasts.

As shown in FIG. 1, tomato rbcS promoter, coding region of a transit peptide and cyanobacterial fructose-1,6-bisphosphatase/sedoheptulose-1,7-bisphosphatase (S.7942 FBP/SBPase) gene (fbp-I) were conjugated with pBI101 to construct a plasmid. The gene named fbp-I indicates a base sequence referred to as base numbers from −180 to 1170 of the sequence number 2, derived from Cyanobacterial synechococcus PCC7942. The plasmid was incorporated into agrobacterium tumefacience LBA4404, which was used for infection of leaf disk of tobacco (Nicotiana tabacum cv Xanthi), to incorporate fbp-1 into a tobacco nuclear gene. After isolating the genomic DNA, incorporation of fbp-1 was confirmed by PCR and immunoblotting methods. 7 strains of transformants (TFI-1 to TFI-7) were obtained. The chloroplasts were isolated from transformed strains (T2 generation), then expression of S.7942 FBPase/SBPase was confirmed by western blotting. Moreover, it was confirmed, by cell fractionation, that the protein expressed from the incorporated gene is localized in the chloroplasts (The FBPase activity, SPBase activity and photosynthetic activity).

The FBPase activity of the blades of the plant body of the transgenic tobacco cultivated 7 weeks after seeding was compared with that of the wild type strain without the incorporated gene. The result showed that the enzyme activity of the wild type strain was 1.04±0.22 $\mu$mol/min/mg chlorophyl and that of the transgenic plant was 1.82±0.24 $\mu$mol/min/mg chlorophyl. Therefore, the activity of the transgenic plant is 1.75 times higher than that of the wild type strain.

The SBPase activity was also compared. The SBPase activity of the wild type strain was 1.37 $\mu$mol/min/mg chlorophyl and that of the transgenic plant was 2.40 $\mu$mol/min/mg chlorophyl. Therefore, the activity of the transgenic plant is 1.75 times higher than that of the wild type strain.

Figure 3:
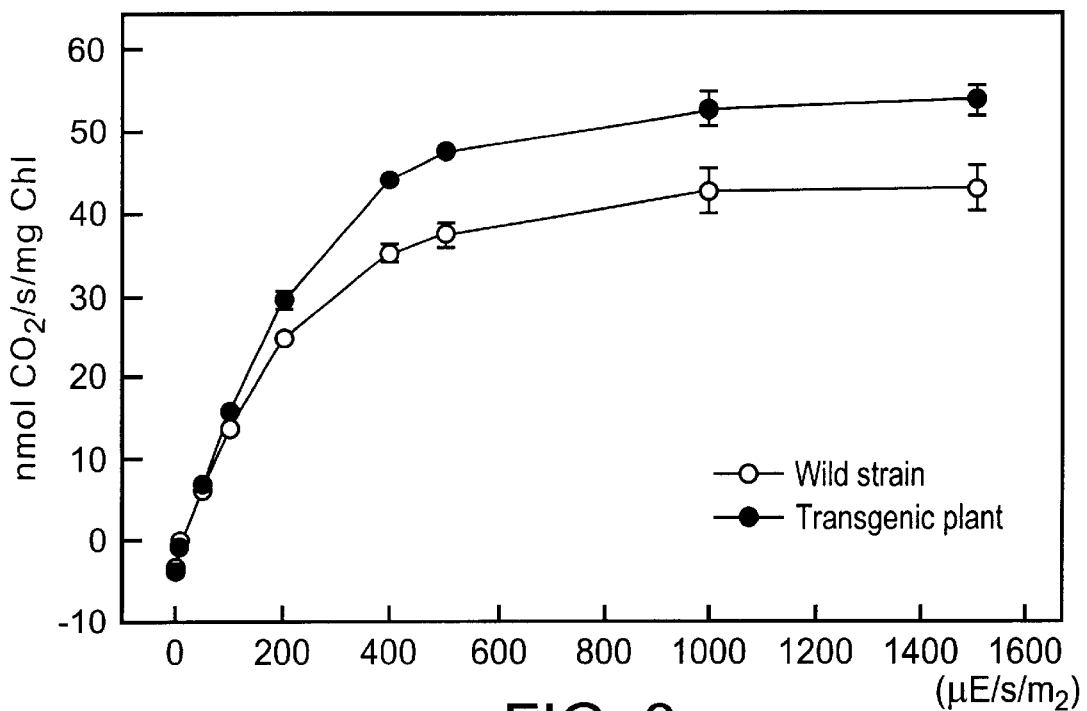
FIG. 3 is a graph showing the photosynthetic ability of a wild type strain and a transgenic plant.

The photosynthetic activity under conventional condition (360 ppm $CO_2$) was compared. As the result, significant difference between the wild type strain and the transgenic plant was not observed under illumination of 0, 10, 50 and 100 $\mu E/s/m^2$. However, the photosynthetic activity of the transgenic plant increased significantly, under illumination of 200 $\mu E/s/m^2$, compared with that of the wild type strain. Under 1600 $\mu E/s/m^2$ of illumination, the enzyme activity of the wild type strain was 1.24 times higher than that of the wild type strain. These results are shown in FIG. 3.

(Effect of Transformation Upon the Plant Growth)

Figure 2:
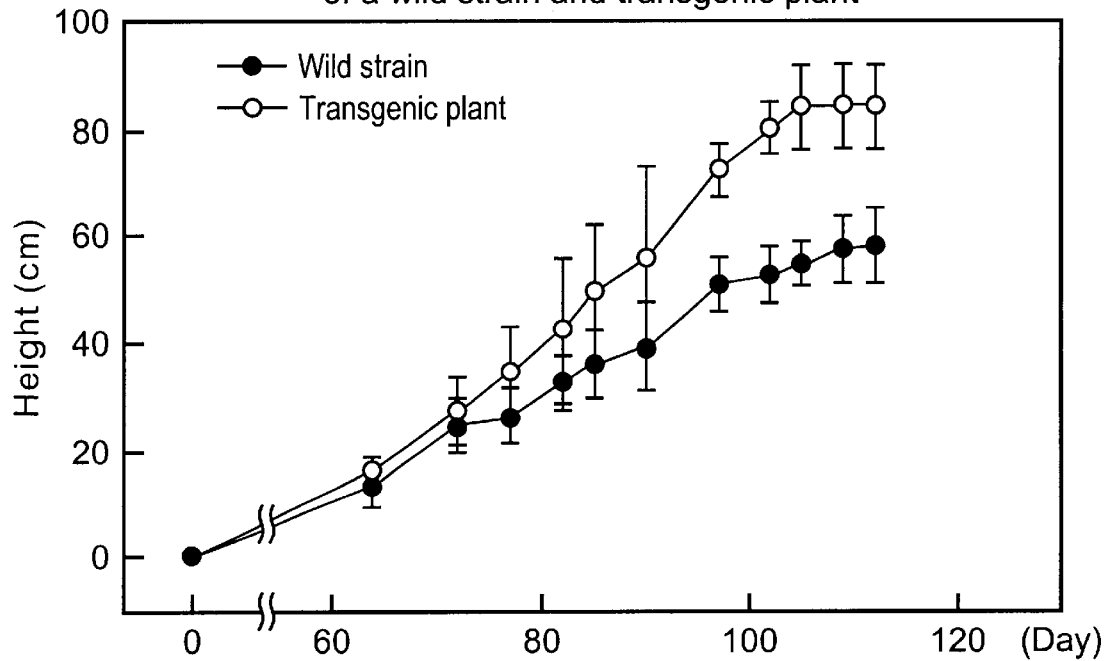
FIG. 2 is a graph showing the heights of the plant bodies of a wild type strain and a transgenic plant under water culture.
Figure 4:
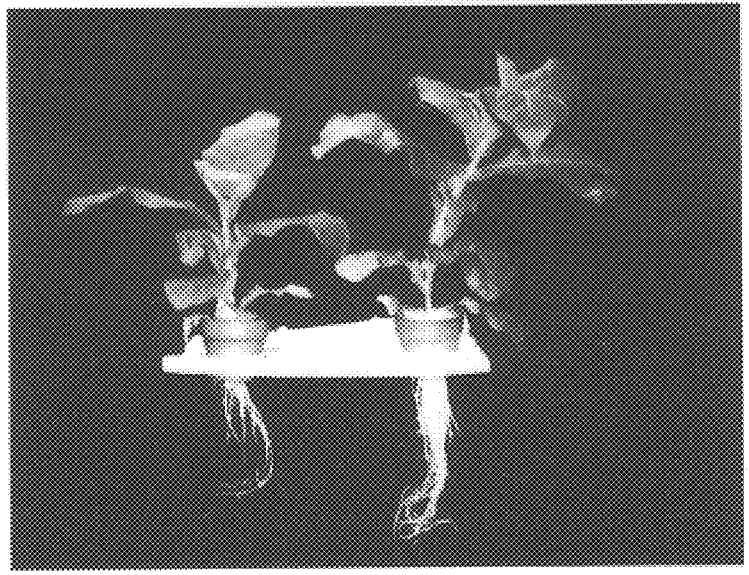
FIG. 4 is a photograph showing appearance of plant bodies of a wild type strain and a transgenic plant, on the 112th day of cultivation under water culture.

Using Hogrant medium, water culture was performed on the wild type strain and the transgenic plant. The experiment was performed under condition of 400 $\mu mol/m^2/s$, a relative humidity of 60% and a temperature of 25° C. On the 63rd day, 72nd day, 77th day, 82nd day, 85th day, 90th day, 97th day, 102nd day, 105th day, 109th day, 112th day of cultivation, the heights of the plant bodies were measured. The results are shown in FIG. 2. On the 64th day of cultivation, the height of the wild type strain was 14.0±4.6 cm and that of the transgenic plant was 16.6±2.9 cm. However, on the 112th day of cultivation, the height of the wild type strain was 58.3±7.0 cm and that of the transgenic plant was 84.5±7.8 cm, indicating significant enhancement of growth in the transgenic plants (about 1.45 times). The pictures in FIG. 4 show plant body of the wild type strain (left) and that of the transgenic plant (right).

Figure 5:
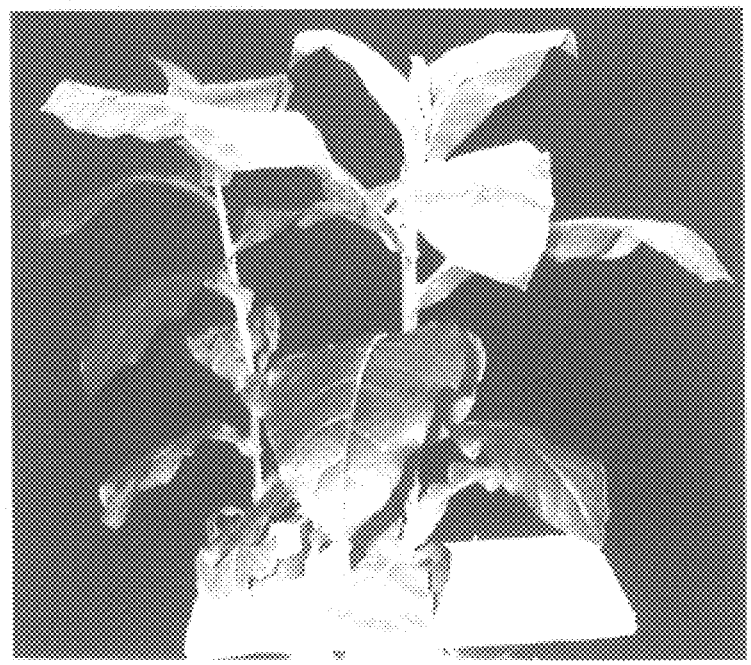
FIG. 5 is a photograph showing the appearance of blades and stems of a wild type strain and a transgenic plant, on the 112th day of cultivation under water culture.
Figure 6:
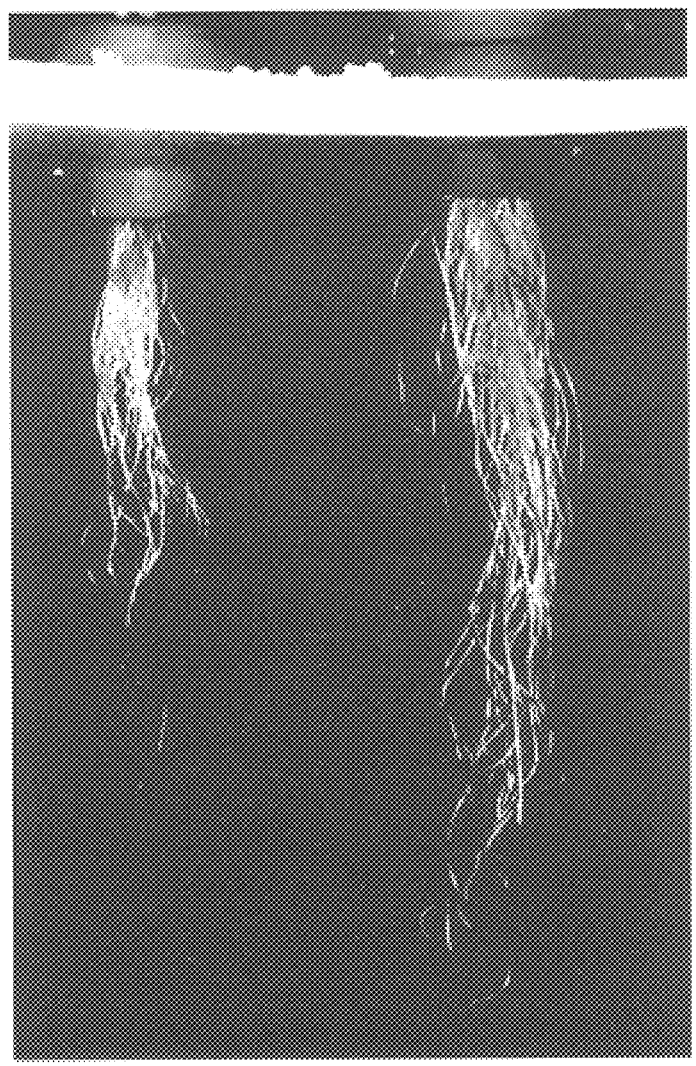
FIG. 6 is a photograph showing the appearance of roots of a wild type strain and a transgenic plant, on the 112th day of cultivation under water culture.

During the whole period of growth, the blades, stems and roots of the transgenic plant grew better than those of the wild type strain. That is, the leaves are thicker with broader surface area, the stems are thicker and the number of roots are larger with each root longer. FIG. 5 is a photograph showing the appearance of the blades and stems on the 112th day of cultivation, and the wild type strain is shown in the left and the transgenic plant is shown in the right. FIG. 6 is a photograph showing the appearance of roots on the 112th day of cultivation, and the wild type strain is shown in the left and the transgenic plant is shown in the right.

(The Contents of Metabolic Intermediates)

Figure 7A:
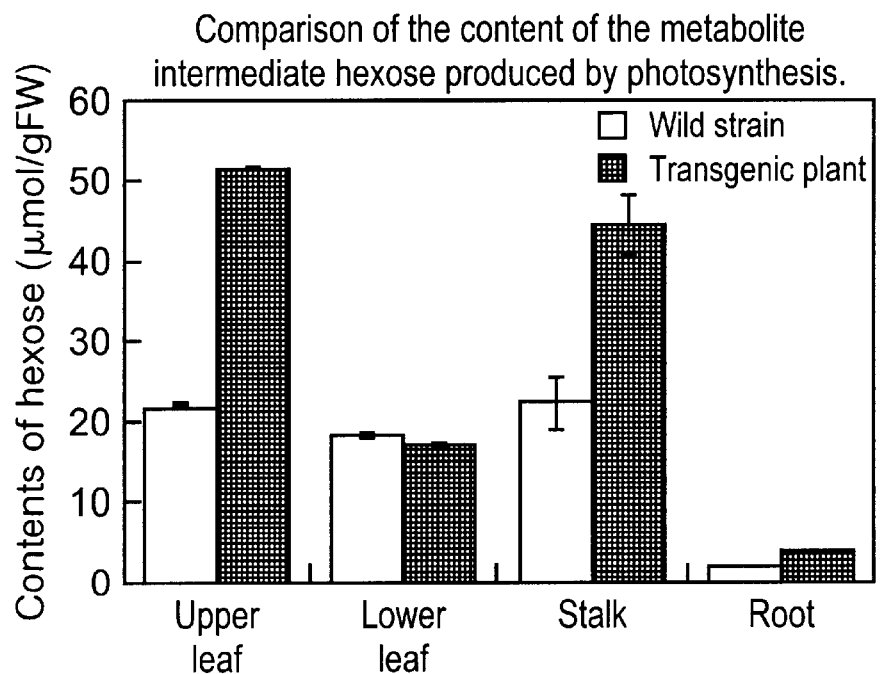
FIGS. 7a, 7b, and 7c are graphs showing the contents of intermediate metabolites of a wild type strain and a transgenic plant.
Figure 7B:
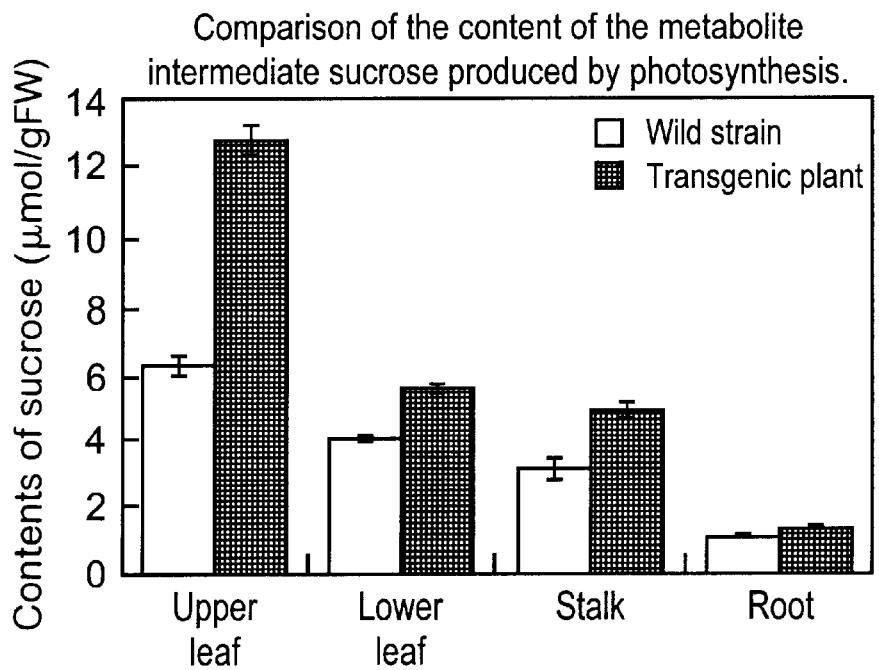
Figure 7C:
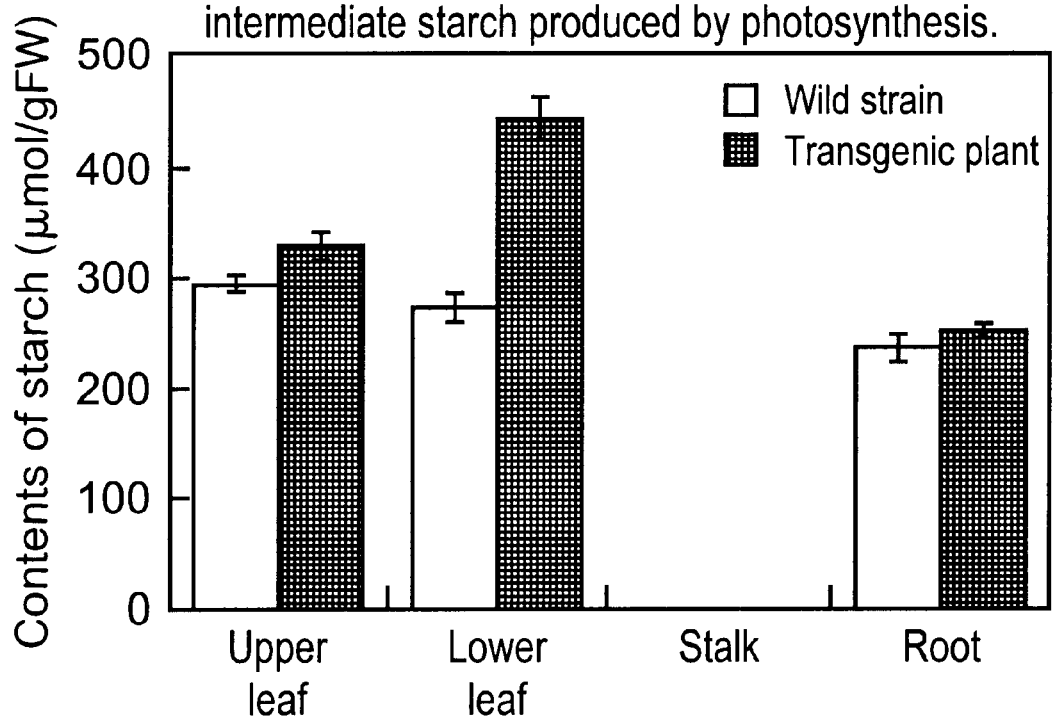

The contents of metabolic intermediates (hexose, sucrose, starch) were measured on upper blades (fourth blade from the top), lower blades (third blade from the bottom), stems and roots of plant bodies 12th week after seeding, for comparing the contents between the wild type strain and the transgenic plant. The results are shown in FIG. 7. The contents of metabolic intermediates in the transgenic plant increased significantly in all parts, including the upper blades, the lower blades, the stems and the roots, compared with the wild type strain. Especially, hexose and sucrose contents in the upper blades considerably increased. The accumulation of starch was observed in the lower blades. This is considered that sucrose synthesized in the upper blades was transferred into the lower blades.

As shown in these results, photosynthesis in higher plants was enhanced by this invention, increasing the production of carbohydrate and starch bio-synthesized in the transgenic plant to promote the plant growth. The dry weight of the plant bodies of the wild type strain was 14.1±2.2 g at the period of flower bud production, and that of the transgenic plant was 21.0±1.9 g. The dry weight of the transgenic plant increased 1.5 times compared with that of the wild type strain, indicating increase of final anabolism.

As described above, photosynthetic ability was enhanced in the transgenic plant of this invention compared with the wild type strain to improve the capability of biosynthesis of carbohydrate and starch, to promote the growth and to increase the final anabolism in the transgenic plant. Accordingly, the incorporation of FBPase/SBPase into chloroplasts of a higher plant is proved to be a very effective technique to produce a rareripe and/or high-yield crop. There has been no technique which enables production of a rareripe and/or high-yield crop using recombinant DNA technique to improve the potosynthetic ability of a higher plant, which is its primary metabolism. Therefore, this invention provides an important key technique to solve the coming crisis of food shortage.

Sequence List
<110>Applicant name: President of Nara institute of science and technology
<120>Title of invention: A method to improve productivity of higher plants transgenic plant
<160>Total number of sequences: 2
<210>Sequence number: 1
<211>Sequence length: 356
<212>Sequence type: PRT
<213>Organism: *Cyanobacterium Synechococcus*
<220>Feature of sequence Topology: linear
Source: fructose-1,6-bisphosphatase/sedoheptulose-1,7-bisphosphatase derived from *Cyanobacterium Synechococcus* PPC 7942 gene <400>Sequence:

| | | |
|---|---|---|
| 1 | M E K T I G L E I I E V V E Q | 15 |
| 16 | A A I A S A R L M G K G E K N | 30 |
| 31 | E A D R V A V E A M R V R M N | 45 |
| 46 | Q V E M L G R I V I G E G E R | 60 |
| 61 | D E A P M L Y I G E E V G I Y | 75 |
| 76 | R D A D K R A G V P A G K L V | 90 |
| 91 | E I D I A V D P C E G T N L C | 105 |
| 106 | A Y G Q P G S M A V L A I S E | 120 |
| 121 | K G G L F A A P D F Y M K K L | 135 |
| 136 | A A P P A A K G K E T S I K S | 150 |
| 151 | A T E N L K I L S E C L D R A | 165 |
| 166 | I D E L V V V V M D R P R H K | 180 |
| 181 | E L I Q E I R Q A G A R V R L | 195 |
| 196 | I S D G D V S A A I S C G F A | 210 |
| 211 | G T N T H A L M G I G A A P E | 225 |
| 226 | G V I S A A A M R C L G G H F | 240 |
| 241 | Q G Q L I Y D P E V V K T G L | 255 |
| 256 | I G E S R E S N I A R L Q E M | 270 |
| 271 | G I T D P D R V Y D A N E L A | 285 |
| 286 | S G Q E V L F A A C G I T P G | 300 |
| 301 | L L M E G V R F F K G G A R T | 315 |
| 316 | Q S L V I S S Q S R T A R F V | 330 |
| 331 | D T V H M F D D V K T V S L P | 345 |
| 346 | L I P D P K W R P E R | 356 |

<110>Applicant name: President of Nara institute of science and technology
<120>Title of invention: A method to improve productivity of higher plants transgenic plant
<160>Total number of sequences: 2
<210>Sequence number: 2
<211>Sequence length: 1350
<212>Sequence type: DNA
<213>Organism: *Cyanobacterium Synechococcus*
<220>Feature of sequence Topology: linear
Source: fructose-1,6-bisphosphatase/sedoheptulose-1,7-bisphosphatase derived from *Cyanobacterium Synechococcus* PPC 7942 gene <400>Sequence:

```
-180  CGTCGCCCGCTCCATGCCCGCAGCTGCGCCTTTGATGCCGCGGAA  -136
-135  GATATTGCCGCCAACTAACGATANNAGTCACTGCGATCGCAACTA   -91
 -90  AAGCCAGAGATGTGAGGAGGGATCCGGCCTTTGGTAGACTCAAC    -46
 -45  TGTTGGAATCCCCAGAAGCAATCATCCGTAAGGAGTCAGGACGGC    -1
   1  GTGGAGAAGACGATCGGTCTCGAGATTATTGAAGTTGTCGAGCAG    45
  46  GCAGCGATCGCCTCGGCCCGCCTGATGGGCAAAGGCGAAAAGAAT    90
  91  GAAGCCGATCGCGTCGCAGTAGAAGCGATGCGGGTGCGGATGAAC   135
 136  CAAGTGGAAATGCTGGGCCGCATCGTCATCGGTGAAGGCGAGCGC   180
 181  GACGAAGCACCGATGCTCTATATCGGTGAAGAAGTGGGCATCTAC   225
 226  CGCGATGCAGACAAGCGGGCTGGCGTACCGGCTGGCAAGCTGGTG   270
 271  GAAATCGACATCGCCGTTGACCCCTGCGAAGGCACCAACCTCTGC   325
 326  GCCTACGGTCAGCCCGGCTCGATGGCAGTTTTGGCCATCTCCGAG   360
 361  AAAGGCGGCCTGTTTGCAGCTCCCGACTTCTACATGAAGAAACTG   405
 406  GCTGCACCCCCAGCTGCCAAAGGCAAAGAGACATCAATAAAGTCC   450
 451  GCGACCGAAAACCTGAAAATTCTCTCGGAATGTCTCGATCGCGCC   495
 496  ATCGATGAATTGGTGGTCGTGGTCATGGATCGTCCCCGCCACAAA   540
 541  GAGCTAATCCAAGAGATCCGCCAAGCGGGTGCCCGCGTCCGTCTG   585
 586  ATCAGCGATGGTGACGTTTCGGCCGCGATCTCCTGCGGTTTTGCT   630
 631  GGCACCAACACCCACGCCCTGATGGGCATCGGTGCAGCTCCCGAG   675
 676  GGTGTGATTTCGGCAGCAGCAATGCGTTGCCTCGGCGGGCACTTC   720
 721  CAAGGCCAGCTGATCTACGACCCAGAAGTGGTCAAAACCGGCCTG   765
 766  ATCGGTGAAAGCCGTGAGAGCAACATCGCTCGCCTGCAAGAAATG   810
 811  GGCATCACCGATCCCGATCGTGTCTACGACGCGAACGAACTGGCT   855
 856  TCGGGTCAAGAAGTGCTGTTTGCGGCTTGCGGTATCACCCCGGGC   900
 901  TTGCTGATGGAAGGCGTGCGCTTCTTCAAAGGCGGCGCTCGCACC   945
 946  CAGAGCTTGGTGATCTCCAGCCAGTCACGGACGGCTCGCTTCGTT   990
 991  GACACCGTTCACATGTTCGACGATGTCAAAACGGTTAGCCTGCCG  1035
1036  TTAATTCCTGATCCCAAATGGCGGCCGGAGCGGTAGAACGGGTAT  1080
1081  AGCTCGATCGCTTCGGTCGTTGTTTTTCAGCGAATCCATTTGCGA  1125
1126  TCGCTTTTCAAACCCTTTTTTCGTCAACCTTCTTTAAACGGCCTC  1170
```

---

What is claimed is:

1. A method for increasing the productivity of a higher plant having chloroplasts, said method comprising:
   a) providing a plasmid comprising a DNA fragment comprising a nucleotide sequence encoding a bifunctional enzyme fructose-1,6-biphosphatase/sedoheptulose-1,7-biphosphatase isolated from *Cynobacterium synechococcus* operably linked to a promoter sequence;
   b) introducing said plasmid into the nuclear genome or chloroplast genome of a callus or a leaf disk; and
   c) regenerating a plant from the callus or leaf disk, wherein said plant exhibits increased productivity by expression of the bifunctional enzyme FBPase/SBPase in said chloroplast.

2. A method for increasing the productivity of a higher plant having chloroplasts, said method comprising:
   a) providing a plasmid comprising a DNA fragment encoding a protein having an amino acid sequence having sequence identity not lower than 95% to the protein having the amino acid sequence of SEQ ID NO:1 operably linked to a promoter sequence; wherein said protein exhibits enzyme activity as a bifunctional enzyme of fructose-1,6-biphosphatase/sedoheptulose-1,7-biphosphatase;
   b) introducing said plasmid into the nuclear genome or chloroplast genome of a callus or a leaf disk; and
   c) regenerating a plant from the callus or leaf disk, wherein said plant exhibits increased productivity by expression of the bifunctional enzyme FBPase/SBPase in said chloroplast.

3. A transgenic plant, wherein said transgenic plant is a higher plant having chloroplasts, the transgenic plant comprising a DNA fragment incorporated in its genome, wherein the DNA fragment comprises a nucleotide sequence encoding a bi-functional enzyme fructose-1,6-biphosphatase/sedoheptulose-1,7-biphosphatase isolated from *Cynobacterium synechococcus*.

4. The transgenic plant according to claim 3, wherein expression of the bi-functional enzyme fructose-1,6-bisphosphatase/sedoheptulose-1,7-bisphosphatase is localized in said chloroplasts.

5. A transgenic plant, wherein said transgenic plant is a higher plant having chloroplasts, the transgenic plant comprising a DNA fragment incorporated in its genome, wherein the DNA fragment comprises a nucleotide sequence encoding a protein having an amino acid sequence having sequence identity not lower than 95% to the protein having the amino acid sequence of SEQ ID NO:1, wherein said protein exhibits enzyme activity as a bifunctional enzyme of fructose-1,6-biphosphatase/sedoheptulose-1,7-biphosphatase.

6. The transgenic plant according to claim 5, wherein said DNA fragment comprises the nucleotide sequence from nucleotides 1 to 1068 of SEQ ID NO:2.

7. The transgenic plant according to claim 6, wherein said DNA fragment comprises (contains) the nucleotide sequence from nucleotides −180 to 1170 of SEQ ID NO:2.

8. The transgenic plant according to claim 5, wherein the expression of said DNA fragment is localized in said chloroplasts.

9. The transgenic plant according to claim 7, wherein the expression of said DNA fragment is localized in said chloroplasts.

10. The transgenic plant according to claim 6, wherein the expression of said DNA fragment is localized in said chloroplasts.

* * * * *

SEQUENCE LISTING

<160> NUMBER OF SEQ ID NOS: 2

<210> SEQ ID NO 1
<211> LENGTH: 356
<212> TYPE: PRT
<213> ORGANISM: Cyanobacterium Synechococcus

<400> SEQUENCE: 1

Met Glu Lys Thr Ile Gly Leu Glu Ile Ile Glu Val Val Glu Gln Ala
 1               5                  10                  15

```
Ala Ile Ala Ser Ala Arg Leu Met Gly Lys Gly Glu Lys Asn Glu Ala
             20                  25                  30
Asp Arg Val Ala Val Glu Ala Met Arg Val Arg Met Asn Gln Val Glu
         35                  40                  45
Met Leu Gly Arg Ile Val Ile Gly Glu Gly Glu Arg Asp Glu Ala Pro
     50                  55                  60
Met Leu Tyr Ile Gly Glu Glu Val Gly Ile Tyr Arg Asp Ala Asp Lys
 65                  70                  75                  80
Arg Ala Gly Val Pro Ala Gly Lys Leu Val Glu Ile Asp Ile Ala Val
                 85                  90                  95
Asp Pro Cys Glu Gly Thr Asn Leu Cys Ala Tyr Gly Gln Pro Gly Ser
             100                 105                 110
Met Ala Val Leu Ala Ile Ser Glu Lys Gly Gly Leu Phe Ala Ala Pro
         115                 120                 125
Asp Phe Tyr Met Lys Lys Leu Ala Ala Pro Pro Ala Lys Gly Lys
     130                 135                 140
Glu Thr Ser Ile Lys Ser Ala Thr Glu Asn Leu Lys Ile Leu Ser Glu
145                 150                 155                 160
Cys Leu Asp Arg Ala Ile Asp Glu Leu Val Val Val Met Asp Arg
                 165                 170                 175
Pro Arg His Lys Glu Leu Ile Gln Glu Ile Arg Gln Ala Gly Ala Arg
             180                 185                 190
Val Arg Leu Ile Ser Asp Gly Asp Val Ser Ala Ala Ile Ser Cys Gly
         195                 200                 205
Phe Ala Gly Thr Asn Thr His Ala Leu Met Gly Ile Gly Ala Ala Pro
     210                 215                 220
Glu Gly Val Ile Ser Ala Ala Ala Met Arg Cys Leu Gly Gly His Phe
225                 230                 235                 240
Gln Gly Gln Leu Ile Tyr Asp Pro Glu Val Val Lys Thr Gly Leu Ile
                 245                 250                 255
Gly Glu Ser Arg Glu Ser Asn Ile Ala Arg Leu Gln Glu Met Gly Ile
             260                 265                 270
Thr Asp Pro Asp Arg Val Tyr Asp Ala Asn Glu Leu Ala Ser Gly Gln
         275                 280                 285
Glu Val Leu Phe Ala Ala Cys Gly Ile Thr Pro Gly Leu Leu Met Glu
     290                 295                 300
Gly Val Arg Phe Phe Lys Gly Gly Ala Arg Thr Gln Ser Leu Val Ile
305                 310                 315                 320
Ser Ser Gln Ser Arg Thr Ala Arg Phe Val Asp Thr Val His Met Phe
                 325                 330                 335
Asp Asp Val Lys Thr Val Ser Leu Pro Leu Ile Pro Asp Pro Lys Trp
             340                 345                 350
Arg Pro Glu Arg
         355

<210> SEQ ID NO 2
<211> LENGTH: 1350
<212> TYPE: DNA
<213> ORGANISM: Cyanobacterium Synechococcus
<220> FEATURE:
<221> NAME/KEY: misc_feature
<222> LOCATION: (69)..(70)
<223> OTHER INFORMATION: Nucleotides at positions 69 and 70 are "n"
      wherein "n" = any nucleotide.

<400> SEQUENCE: 2
```

-continued

```
cgtcgcccgc tccatgcccg cagctgcgcc tttgatgccg cggaagatat tgccgccaac        60
taacgatann agtcactgcg atcgcaacta aagccagaga tgtgaggagg ggatccggcc        120
tttggtagac tcaactgttg gaatccccag aagcaatcat ccgtaaggag tcaggacggc        180
gtggagaaga cgatcggtct cgagattatt gaagttgtcg agcaggcagc gatcgcctcg        240
gcccgcctga tgggcaaagg cgaaaagaat gaagccgatc gcgtcgcagt agaagcgatg        300
cgggtgcgga tgaaccaagt ggaaatgctg ggccgcatcg tcatcggtga aggcgagcgc        360
gacgaagcac cgatgctcta tatcggtgaa gaagtgggca tctaccgcga tgcagacaag        420
cgggctggcg taccggctgg caagctggtg gaaatcgaca tcgccgttga ccctgcgaa        480 ggcaccaacc tctgcgccta cggtcagccc ggctcgatgg cagttttggc catctccgag        540
aaaggcggcc tgtttgcagc tcccgacttc tacatgaaga aactggctgc accccagct         600 gccaaggca aagagacatc aataaagtcc gcgaccgaaa acctgaaaat tctctcggaa         660
tgtctcgatc gcgccatcga tgaattggtg gtcgtggtca tggatcgtcc ccgccacaaa        720
gagctaatcc aagagatccg ccaagcgggt gcccgcgtcc gtctgatcag cgatggtgac        780
gtttcggccg cgatctcctg cggttttgct ggcaccaaca cccacgccct gatgggcatc        840
ggtgcagctc ccgagggtgt gatttcggca gcagcaatgc gttgcctcgg cgggcacttc        900
caaggccagc tgatctacga cccagaagtg gtcaaaaccg gcctgatcgg tgaaagccgt        960
gagagcaaca tcgctcgcct gcaagaaatg ggcatcaccg atcccgatcg tgtctacgac       1020
gcgaacgaac tggcttcggg tcaagaagtg ctgtttgcgg cttgcggtat caccccgggc       1080
ttgctgatgg aaggcgtgcg cttcttcaaa ggcggcgctc gcacccagag cttggtgatc       1140
tccagccagt cacggacggc tcgcttcgtt gacaccgttc acatgttcga cgatgtcaaa       1200
acggttagcc tgccgttaat tcctgatccc aaatggcggc cggagcggta gaacgggtat       1260
agctcgatcg cttcggtcgt tgtttttcag cgaatccatt tgcgatcgct tttcaaaccc       1320
ttttttcgtc aaccttcttt aaacggcctc                                        1350
```